United States Patent [19]

Wang et al.

[11] Patent Number: 4,544,546

[45] Date of Patent: Oct. 1, 1985

[54] FLUORESCENT NUCLEIC ACID STAINS

[75] Inventors: Chao-Huei J. Wang, Gurnee; Michael E. Jolley, Round Lake, both of Ill.

[73] Assignee: Abbott Laboratories, North Chicago, Ill.

[21] Appl. No.: 510,506

[22] Filed: Jul. 5, 1983

Related U.S. Application Data

[60] Division of Ser. No. 278,812, Jun. 29, 1981, abandoned, which is a continuation-in-part of Ser. No. 142,321, Apr. 21, 1980, abandoned.

[51] Int. Cl.$^4$ .......................... C12Q 1/68; G01N 1/00; G01N 31/00
[52] U.S. Cl. .......................................... 424/7.1; 424/3; 435/6; 436/63; 436/94
[58] Field of Search .................. 424/3, 7.1; 435/6; 436/63, 94

[56] References Cited

U.S. PATENT DOCUMENTS 3,833,863  9/1974  Webster et al. ..................... 372/53

OTHER PUBLICATIONS

Chemical Abstracts, I, 15: 148184, (1977).
Chemical Abstracts, II, 68: 1825, (1978).
Chemical Abstracts, III, 57: 211861, (1982).

Primary Examiner—Sidney Marantz
Assistant Examiner—L. Krawczewicz
Attorney, Agent, or Firm—James L. Wilcox; Martin L. Katz

[57] ABSTRACT

This disclosure relates to a class of compounds which are utilized as biological stains in fluorescent microscopy. In particular, the disclosure relates to a method for detecting and identifying various structures in a biological sample which comprises treating said biological sample with a compound of the present disclosure to form a complex which emits fluorescence when irradiated with incident light. This class of compounds has been shown to be useful in detecting a variety of structures such as, for example, viruses, bacteria, yeasts, fungi, reticulocytes and cells in biological samples.

18 Claims, No Drawings

FLUORESCENT NUCLEIC ACID STAINS

This is a division of application Ser. No. 278,812, filed June 29, 1981, now abandoned, which was a continuation-in-part of application Ser. No. 142,321, filed Apr. 21, 1980, now abandoned.

BACKGROUND OF THE INVENTION

1. Field of the Invention

This invention relates generally to the technique of fluorescence microscopy which has developed recently into a valuable tool for biological research. Fluorescence microscopy is an extraordinary sensitive method for detecting low concentrations of a substance which comprises treating the substance with a dye to produce a complex which fluoresces when excited with incident light. More particularly, this disclosure relates to a method of detecting qualitatively and/or quantitatively a variety of organisms in biological samples. The detection of said organisms is facilitated by the nucleic acid staining properties of the disclosed dyes.

2. Description of the Prior Art

A variety of compounds have been used in fluorescent microscopy histology and fluorescence microfluorimetry to selectively stain nucleic acids. Von Bertalanffy and Bickis, J. Histochem., Cytochem., Vol. 4, pp. 481–493 (1956), reported that acridine orange could be used for the identification of cytoplasmic basophilia (RNA) by fluorescence microscopy. In particular, they found that acridine orange enables identification of basophilic cytoplasmic inclusions in the supravital state, and that the red fluorescent cytoplasmic inclusions correspond to those stained with the toluidine blue technique and shown by ribonuclease to consist mainly of RNA.

Rosell, et al reported in Nature, Vol. 253, p. 461, (1975) that 4'6-diamidini-2-phenylindole (DAPI) has been shown to possess useful DNA binding properties. Specifically, they found that DAPI can be used as a highly specific fluorescent stain for both nuclear and mitochondrial DNA in yeast.

Hilwig and Gropp in Experimental Cell Research, 75, pp. 122–126 (1972) discuss a simple and direct fluorescence staining procedure using a benzimidazole derivative (identified as 33258 Hoechst) to visualize chromosomal segments to heterchromatin and (in the mouse) sites of repetitious DNA.

However, there are various disadvantages associated with the prior art dyes that are employed in fluorescent microscopy and related techniques. The complexes produced by conventionally employed dyes have limited excitation/emission spectra, low quantum yields, high background fluorescence, low fluorescent enhancement and most importantly such dye complexes are not permanent but rather tend to fade and bleach. In addition, most of the prior art dyes have a high degree of fluorescence in the free, uncomplexed state and are relatively unstable when exposed to light. For example, complexes produced as a result of treating DNA with acridine orange exhibit a fluorescent enhancement only twice as great as acridine orange in the free uncomplexed state. In addition, DAPI and Hoechst 33258, although producing complexes having detectable fluorescent enhancements when bound to DNA, require ultraviolet excitation and emit a blue fluorescence thereby increasing the difficulty of observing such complexes using fluorescent microscopy. There exists a need in fluorescent microscopy and related techniques for a class of dyes essentially nonfluorescent in the free, uncomplexed state and capable of forming highly fluorescent complexes when bound to cellular components, in particular, nucleic acids. It is further desired that such complexes have low background fluorescence, a high degree of fluorescent enhancement and be preferably metachromic and permanent.

Some of the compounds utilized in the method of the present invention have been described as laser dyes in U.S. Pat. No. 3,833,863 and as photographic dyes in Defensive Publication T88 9016. However, neither reference discloses nor suggests the use of these compounds as proposed in the present invention.

SUMMARY OF THE INVENTION

The present invention relates to a novel method of detecting nucleic acids in a biological sample which comprises producing a dye complex by treating said biological sample with an effective amount of dye of the formula:

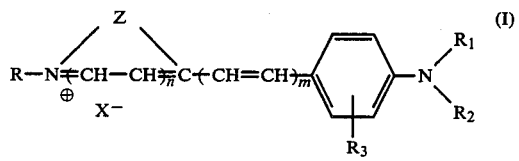

wherein n represents an integer having a value of 0 or 1;
m represents an integer having a value of 1 or 2;
R represents a member selected from the group consisting of lower alkyl, lower hydroxyalkyl, dialkylaminoalkyl, pyrrolidinoalkyl and morpholinoalkyl;
$R_1$ and $R_2$ each represent members selected from the group consisting of hydrogen, lower alkyl and lower haloalkyl;
$R_3$ represents a member selected from the group consisting of hydrogen, lower alkoxy, lower alkyl and amino;
Z represents nonmetallic atoms necessary to complete a heterocyclic nucleus selected from the group consisting of a benzothiazole nucleus, indolenino nucleus, naphthothiazole nucleus, benzoselenazole nucleus, benzoxazole nucleus, quinoline nucleus, and pyridine nucleus any of which may be substituted with lower alkyl, halo, nitro, amino and dialkylamino; and
X represents an anion; irradiating the dye complex with light of excitation wavelength thereby causing the dye complex to emit fluorescence; and measuring the emitted fluorescence.

The present invention further relates to a novel class of compounds of the formula:

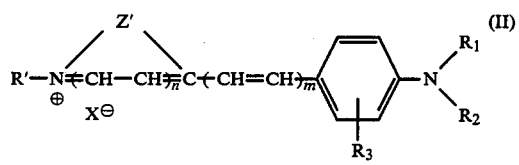

wherein n, m, $R_1$, $R_2$, $R_3$ and X are above-defined; R' is dialkylaminoalkyl and Z' represents nonmetallic atoms necessary to complete a pyridine nucleus; and to methods of using such compounds as tissue stains.

In addition, the present invention also relates to a novel class of compounds of the formula:

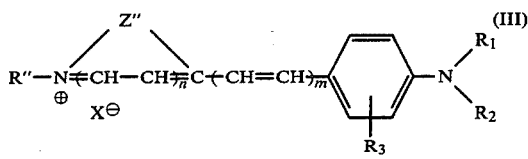

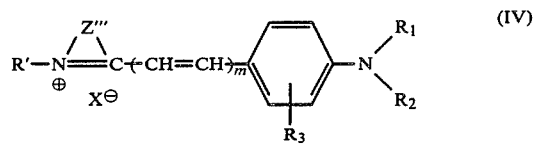

wherein n, m, $R_1$, $R_2$, $R_3$ and X are above defined; R" is lower alkyl and Z" represents nonmetallic atoms necessary to complete an aminopyridine nucleus and to methods of using such compounds as stains for living cells.

Illustrative of the anions represented by X includes halogens such as chloride, iodide and bromide, methylsulfate, perchlorate and the like. It is preferred to employ iodide or methylsulfate.

DESCRIPTION OF THE PREFERRED EMBODIMENT

In general, when a biological sample is treated with a dye of formula (I), a complex is produced which emits fluorescence when irradiated with light of an appropriate excitation wavelength. Observation of the fluorescence enables one to detect and identify various structural features of the sample.

The dyes of formula (I) are essentially nonfluorescent in aqueous solutions, but show marked fluorescent enhancements when bound to various cellular components, in particular, when bound to double stranded DNA. The term "fluorescent enhancement" as used herein, refers to the increase in fluorescence that is emitted by a dye complex when irradiated with respect to the fluorescence emitted by the dye when irradiated in its free or "uncomplexed" state. It has been noted that the degree of fluorescent enhancement for the compounds of formula (I) has been found to be unexpectedly greater than the fluorescent enhancement for most of the dyes disclosed in the prior art that are employed in fluorescent microscopy. Also, because of the relative nonfluorescence properties of the dyes of the present invention when irradiated in a free or "uncomplexed" state, large quantities of the dyes may be employed without having to separate or remove excess reagent. This is of particular importance in applications wherein poor absorption of the dye by the biological sample occurs. In addition, because of the high fluorescence quantum yield of some of the complexes formed, small quantities of dye may be employed. It is important to note that the properties of the complexes produced using the dyes of formula (I) are for the most part not pH or concentration dependent.

The dyes of formula (I) are relatively soluble and extremely stable in aqueous solutions. This solubility in aqueous solutions enables one to eliminate organic solvents which are generally undesirable when working with living cells. The stability of the dyes of the present invention in aqueous solutions with respect to light provides the dyes with a longer shelf-life than is normally expected with fluorescent biological stains. In addition, unlike most commonly available dyes which are mixtures of various compounds, the dyes of the present invention are generally pure materials, and thus are readily characterized. This is of particular importance in reducing the time and expense necessary to characterize different lots of the dyes.

It has been found that a class of dyes of the formula:

wherein m, $R_1$, $R_2$, $R_3$, R' and X are above defined and Z''' represents nonmetallic atoms necessary to complete a heterocyclic nucleus selected from the group consisting of a benzothiazole nucleus, a naphthothiazole nucleus, a benzoselenazole nucleus, a benzoxazole nucleus or a substituted benzothiazole, naphthothiazole, benzoselenazole nucleus wherein the substituent is selected from the class consisting of lower alkyl, amino and halo; are "specific stains" for DNA. That is, under general conditions, when a biological sample is treated with a dye of formula (IV), the dye preferably forms a dye complex with DNA, thereby providing a specific means of detecting and identifying DNA. As a result of this tendency to preferably bind DNA rather than RNA or other cellular structures, the dye of formula (IV) are unexpectedly and extremely useful in detecting and identifying bacteria and white cells. It has also been found that certain dyes of formula (IV), in particular, those dyes wherein Z''' represents nonmetallic atoms necessary to complete an aminobenzothiazole nucleus are effective stains when cellular identification techniques are employed, i.e., cancer screening.

It is preferred to employ dyes of formula (IV) wherein m is 1, $R_1$ and $R_2$ are lower alkyl, $R_3$ is hydrogen and Z''' represents nonmetallic atoms necessary to complete a heterocyclic nucleus selected from the group consisting of a benzothiazole nucleus, a naphthothiazole nucleus, an aminobenzothiazole nucleus and aminonaphthothiazole nucleus as "specific stains" for DNA. It is more preferred to employ dyes of formula (I) wherein $R_1$ and $R_2$ are either methyl or ethyl, R' is dimethylaminopropyl or diethylaminopropyl, and Z''' represents nonmetallic atoms necessary to complete a benzothiazole or an aminobenzothiazole nucleus as "specific stains" for DNA. It is most preferred to employ 3-γ-dimethylaminopropyl-2-p-dimethyl aminostyrylbenzothiazolium iodide.

The dyes of formula (II) are characterized as "nonspecific" stains for tissues and fixed cells. That is, in addition to staining nucleic acids, DNA and RNA, the dyes of formula (II) are also effective in staining other cellular structures and in particular endoplasmic reticulum, lipids and hydrophobic proteins. The dyes of formula (II) are of particular importance because in addition to possessing the properties mentioned above, the dyes of formula (II) have been unexpectedly found to be "metachromatic" and "permanent". By "metachromatic" is meant that when a tissue or fixed cell sample is treated with a dye of formula (II), the various structures of the sample produce complexes which emit fluorescence of varying colors, thereby increasing the ability to detect and identify the individual structures of interest. By "permanent" is meant the dye complexes produced by treating the various cellular structures with a dye of formula (II) will emit fluorescence whose color will not bleach or fade over a long period of time. These unexpected and extremely significant properties possessed by the dyes of formula (II), enable these dyes to be superior stains for detecting various cellular features such as chromatin and the size and shape of the nucleus and distinguishing between normal and abnormal cells in tissues and fixed cells. It is of particular importance that the dyes of formula (II) have the ability to form "permanent" dye complexes because fading of a preparation either before, during or between observations or measurements leads to errors in the detection or the quantification of structures. Applications of the dyes of formula (II) include reticulocyte differentiation from erythrocytes, differentiation of white cell classes and discrimination between abnormal and normal cells.

The preferred "nonspecific stains" for tissues and fixed cells include dyes of formula (II) wherein m is 1, $R_1$ and $R_2$ are lower alkyl and $R_3$ is hydrogen. It is most preferred that n is 1, $R_1$ and $R_2$ are methyl or ethyl and R' is dimethylaminopropyl or diethylaminopropyl. It is most preferred to employ 1-γ-dimethylaminopropyl-4-p-dimethylaminostyrylpyridinium iodide as a "nonspecific stain" for tissue and "fixed cell" samples.

The dyes of formula (III) are characterized as "nonspecific" stains for samples containing "cells in suspension" or so-called "living cells". Unlike the specific DNA dyes of formula (IV) or the nonspecific tissue and fixed cell dyes of formula (II), the dyes represented by formula (III) have been found to be unexpectedly effective supravital stains. This is due in part to the fact that the dyes of formula (III) readily penetrate the cell membrane without killing the cell. This ability to stain living cells has important applications in flow cytofluorimetry systems.

The preferred "nonspecific" stains for samples containing "cells in suspension" or "living cells" includes dyes of formula (III) wherein m is 1, $R_1$ and $R_2$ are lower alkyl and $R_3$ is hydrogen. It is more preferred that n is 1 and $R_1$, $R_2$ and R' are methyl or ethyl. It is most preferred to employ 1-methyl-2-amino-4-p-dimethylaminostyrylpyridinium iodide as a nonspecific stain for living cells.

The dyes of the present invention may be prepared in accordance with the following general procedure:

A compound of the formula:

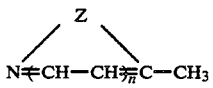  (V)

wherein Z and n are above defined is treated with a halide of the formula:

R—X                                                                  (VI)

wherein R and X are above defined to yield a quaternary intermediate of the formula:

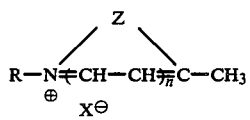  (VII)

The quaternary intermediate of formula (VII) is subsequently treated with a substituted aminobenzaldehyde of the formula:

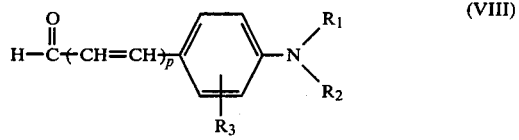  (VIII)

wherein $R_1$, $R_2$, and $R_3$ are above defined and p=n−1; to yield the dyes of formula (I).

The following examples serve to further illustrate the present invention. All parts are parts by weight unless otherwise expressly set forth.

EXAMPLE 1

In a one liter flask, 10.3 g of 3-dimethylamino-1-propanol (0.1 mol) was slowly added to 19 g of p-toluene sulfonyl chloride (0.1 mol) with cooling and stirring for ten minutes to yield a solid residue. The residue was dissolved in 200 ml of acetone. To the acetone solution was added a solution containing 30 g of sodium iodide (0.2 mol) in 200 ml of acetone. The resulting mixture was refluxed for one hour and then cooled to room temperature to yield a white precipitate. The reaction mixture was filtered, and the white precipitate was washed with acetone. The filtrate was evaporated to yield 30 g of 3-dimethylamino-1-iodopropane hydroiodide as a yellowish heavy oil which partially solidified on standing, and was further used without purification.

A mixture containing 0.3 g of 2-methylbenzothiazole (0.002 mol) and 0.68 g of 3-dimethylamino-1-iodopropane hydroiodide (0.002 mol) was heated within a temperature range of 120°–130° C. for two hours to yield a quaternary salt intermediate. The quaternary salt intermediate was washed with ether and then refluxed with a solution containing 0.3 g of p-dimethylaminobenzaldehyde (0.002 mol) in 10 ml of acetic anhydride for 30 minutes, cooled, filtered and rinsed with acetone to yield 3-γ-dimethylaminopropyl-2-p-dimethylaminostyrylbenzothiazoline iodide (Dye No. 1) (0.65 g; 66% yield) as a solid having a melting point of 241°–243° C. (dec.).

EXAMPLE 2

A mixture containing 3-dimethylamino-1-iodopropane hydroiodide (0.68 g; 0.002 mol) and excess 4-picoline (0.28 g; 0.003 mol) was heated within a temperature range of 120°–130° C. for two hours to yield a quaternary salt. The quaternary salt was then rinsed with either. To the quaternary salt was added p-dimethylaminobenzaldehyde (0.3 g; 0.002 mol), 0.5 ml of piperidine and 10 ml of ethanol and the resulting mixture was refluxed for thirty minutes. Ether was added to the reaction mixture to precipitate a crude product. The ether was decanted from the reaction mixture and the remaining crude product was treated with acetone. The crude product-acetone mixture was filtered to yield 1-γ-dimethylaminopropyl-4-p-dimethylaminostyrylpyridinium iodide (0.4 g.; 46% yield) (Dye No. 28) as a crystalline precipitate having a melting point of 134°–140° C.

EXAMPLE 3

A mixture containing 2-amino-4-picoline (21.6 g; 0.1 mol) and dimethylsulfate (12.6 g; 0.1 mol) was heated within a temperature range of 100°–120° C. for one hour to yield a quaternary ammonium salt. To the quaternary ammonium salt was added p-dimethylaminobenzaldehyde (14.9 g; 0.1 mol), 10 ml of piperidine and 100 ml of methanol. The resulting mixture was refluxed for one hour and poured into a solution containing 20 g of potassium iodide in 200 ml of water to yield a precipitate. The solution was filtered, the precipitate rinsed briefly with water and recrystallized from ethanol to yield 1-methyl-2-amino-4-p-dimethylaminostyrylpridinium iodide (Dye No. 33) (20.4 g; 50% yield) having a melting point of 242°–244° C.

In accordance with the procedures described above, the following dyes have been prepared and employed in the methods of the present invention:

| Dye No. | Chemical Name | m.p. (°C.) |
|---|---|---|
| 1 | 3-γ-dimethylaminopropyl-2-p-dimethylaminostyrylbenzothiazolium iodide | 241–243 |
| 2 | 3-γ-dimethylaminopropyl-2-p-dimethylaminostyrylbenzoxazolium iodide | 237–239 |
| 3 | 1-γ-dimethylaminopropyl-2-p-dimethylaminostyryl-3,3-dimethyl-3H—indolium iodide | 220–230 |
| 4 | 3-methyl-6-dimethylamino-2-p-dimethylaminostyrylbenzothiazolium iodide | 244–247 |
| 5 | 3-β-dimethylaminoethyl-2-p-dimethylaminostyrylbenzothiazolium iodide | 227–230 |
| 6 | 3-γ-dimethylaminopropyl-2-p-diethylaminostyrylbenzothiazolium iodide | 195–197 |
| 7 | 3-γ-dimethylaminopropyl-5-chloro-2-p-dimethylaminostyrylbenzothiazolium iodide | 256–258 |
| 8 | 3-γ-dimethylaminopropyl-2-p-dimethylaminostyryl-γ-naphthothiazolium iodide | 260–265 |
| 9 | 3-γ-dimethylaminopropyl-2-p-dimethylaminostyrylbenzoselenazolium iodide | 257–258 |
| 10 | 3-γ-dimethylaminopropyl-5-methyl-2-p-dimethylaminostyrylbenzothiazolium iodide | 253–256 |
| 11 | 3-β-diethylaminoethyl-2-p-dimethylaminostyrylbenzothiazolium iodide | 248–250 |
| 12 | 3-γ-dimethylaminopropyl-2-p-(N—2-chloroethyl-N—ethyl)-aminostyrylbenzothiazolium iodide | 157–150 |
| 13 | 3-γ-dimethylaminopropyl-2-p-N,N—bis-(2-chloroethyl)-amino-o-methylstyrylbenzothiazolium iodide | 175–180 |
| 14 | 3-γ-dimethylaminopropyl-2-p-N,N—bis-(2-chloroethyl)-aminostyrylbenzothiazolium iodide | 155–160 |
| 15 | 3-(β-pyrrolidinoethyl)-2-p-dimethylaminostyrylbenzothiazolium iodide | 199–201 |
| 16 | 3-(β-morpholinoethyl)-2-p-dimethylaminostyrylbenzothiazolium iodide | 249–250 |
| 17 | 3-γ-dimethylaminopropyl-2-(4-p-dimethylaminophenyl-1,3-butadienyl)-benzothiazolium iodide | 230–235 |
| 18 | 3-γ-dimethylaminopropyl-2-(4-p-dimethylaminophenyl-1,3-butadienyl)-benzoxazolium iodide | 200–202 |
| 19 | 3-γ-dimethylaminopropyl-2-(4-p-dimethylaminophenyl-1,3-butadienyl)-5-methylbenzothiazolium iodide | 190–195 |
| 20 | 3-γ-dimethylaminopropyl-2-(4-p-dimethylaminophenyl-1,3-butadienyl)-α-naphthothiazolium iodide | 226–228 |
| 21 | 3-γ-dimethylaminopropyl-2-(4-p-dimethylaminophenyl-1,3-butadienyl-5-chlorobenzothiazolium iodide | 222–224 |
| 22 | 3-γ-dimethylaminopropyl-2-(4-p-dimethylaminophenyl-1,3-butadienyl)-6-nitrobenzothiazolium iodide | 250–255 |
| 23 | 3-γ-dimethylaminopropyl-2-(4-p-dimethylaminophenyl-1,3-butadienyl)-benzoselenazolium iodide | 218–220 |
| 24 | 3-γ-diethylaminopropyl-2-(4-p-dimethylaminophenyl-1,3-butadienyl)-benzothiazolium iodide | 230–232 |
| 25 | 1-γ-dimethylaminopropyl-4-p-dimethylaminostyrylquinolinium iodide | 180–185 |
| 26 | 1-γ-dimethylaminopropyl-2-p-dimethylaminostyrylquinolinium iodide | 237–240 |
| 27 | 1-γ-dimethylaminopropyl-4-(4-p-dimethylaminophenyl-1,3-butadienyl)-quinolinium iodide | 203–205 |
| 28 | 1-γ-dimethylaminopropyl-4-p-dimethylaminostyrylpyridinium iodide | 134–140 |
| 29 | 3-propyl-2-p-dimethylaminostyrylbenzothiazolium iodide | 256–257 |
| 30 | 1-ethyl-4-p-diethylaminostyrylquinolinium iodide | 198–199 |
| 31 | Anhydro-3-γ-sulfopropyl-2-p-dimethylaminostyrylbenzothiazolium hydroxide | 296–297 |
| 32 | 3-β-carboxyethyl-2-p-dimethylaminostyrylbenzothiazolium iodide | 210–212 |
| 33 | 1-methyl-2-amino-4-p-dimethylaminostyrylpyridinium iodide | 242–244 |
| 34 | 1-methyl-2-amino-4-p-diethylaminostyrylpyridinium iodide | 194–195 |
| 35 | 1-ethyl-2-amino-4-p-diethylaminostyrylpyridinium iodide | 201–204 |
| 36 | 1-methyl-2-amino-4-p-N,N—bis-(2-chloroethyl)-aminostyrylpyridinium iodide | 210–214 |
| 37 | 1-methyl-2-amino-4-p-N,N—bis-(2-chloroethyl)-amino-o-methylstyrylpyridinium iodide | 250–252 |
| 38 | 1-ethyl-2-amino-4-p-dimethylaminostyrylpyridinium iodide | 235–236 |
| 39 | 1-methyl-2-amino-4-(4-p-dimethylaminophenyl-1,3-butadienyl)-pyridinium iodide | 180–186 |
| 40 | 1-methyl-4-amino-4-(p-dimethylaminostyryl)quinolinium iodide | 293–295 |
| 41 | 1-ethyl-4-amino-2-(p-dimethylaminostyryl)quinolinium methyl sulfate | 230–232 |
| 42 | 1-ethyl-4-amino-2-(p-diethylaminostyryl)quinolinium methyl sulfate | 180–183 |
| 43 | 1-β-hydroxyethyl-4-amino-2-(p-dimethylaminostyryl)quinolinium methyl sulfate | 248–250 |
| 44 | 1-γ-dimethylaminopropyl-2-(p-dimethylaminostyryl)pyridinium iodide | 205–210 |
| 45 | 1-methyl-4-(p-dimethylaminostyryl)-pyridinium iodide | 247–249 |
| 46 | 1-methyl-4-(p-dimethylaminophenyl-1,3-butadienyl)pyridinium iodide | 235–241 |
| 47 | 1-methyl-2-(-p-dimethylaminostyryl)-pyridinium iodide | 251–254 |
| 48 | 1-methyl-2-(4-p-dimethylaminophenyl-1,3-butadienyl)pyridinium iodide | 225–226 |
| 49 | 1-methyl-4-(p-dimethylaminostyryl)-pyridinium iodide | 109–110 |

EXAMPLE 4

A solution containing 0.1 μM of Dye No. 1 in 3 ml. of a 0.01M phosphate buffered saline (PBS) solution having a pH of 7.3 was irradiated with light. The excitation wavelength was determined and the fluorescence emitted was measured using a Perkin Elmer MPF 43-A Fluorescence Spectrophotometer.

Samples containing 100 μg per ml. of calf thymus type I DNA were stained with the PBS-dye solution. The samples were irradiated with light at the excitation wavelength and the emitted fluorescence was measured. The fluorescent enhancement for DNA was calculated as the ratio of the fluorescence emitted by the stained DNA sample to the fluorescence emitted by the PBS-day solution.

Samples containing 100 μg per ml. of yeast type III RNA were stained with the PBS-dye solution. The samples were irradiated with light at the excitation wavelength and the emitted fluorescence was measured. The fluorescent enhancement for RNA was calculated as the ratio of the fluorescence emitted by the stained RNA sample to the fluorescence emitted by the PBS-dye solution.

The above procedures were repeated for Dyes Nos. 1–38 listed above and the results are recorded in Table I. In addition, the relative-fluorescence of each dye with respect to Dye No. 1, i.e., the ratio of the fluorescence emitted by a sample of DNA stained with a particular dye to the fluorescence emitted by a sample of DNA stained with Dye No. 1; was calculated and recorded in Table I.

The concentrations of the dye solutions employed in the methods of the present invention are readily ascertained by one of ordinary skill in the art and vary depending on the type of sample to be stained, the method of staining, the method of detection and the specific dye employed. It has been found that concentrations in a range of 1–200 μg/ml are generally satisfactory in the methods of the present invention. Although aqueous dye solutions are preferred, any solvent in which the dyes of formula (I) are sufficiently soluble may be employed.

staining was observed in the erythrocytes or in the cytoplasm of the PBLs.

EXAMPLE 6

20 μl of a solution of Dye No. 1 (2 mg/ml in 0.9% saline) was added to 2 ml of a suspension of E. coli ($10^8$–$10^9$ cells ml). The mixture was vortexed and a wet slide prepared and examined as described in Example 5. The stained bacteria were observed as brilliant orange rods against a black background.

EXAMPLE 7

To 2 ml of a suspension of E. coli ($\sim 10^9$ cells per ml) was added 20 μl of a 2 mg/ml solution of Dye No. 25. The mixture was shaken and a wet slide prepared and examined as in Example 5. The stained bacteria were observed as brilliant red rods on a black background.

EXAMPLE 8

TABLE I

| Dye | λ Excitation (nm) | λ Emission (nm) | Enhancement In Fluorescence | | Relative Fluorescence Of Dye In DNA Solution |
|---|---|---|---|---|---|
| | | | Dye + DNA/Dye | Dye + RNA/Dye | |
| 1 | 550 | 595 | 121 | 15 | 1 |
| 2 | 530 | 568 | 22 | 9 | 0.15 |
| 3 | 560 | 598 | 3 | 1 | 0.08 |
| 4 | 560 | 600 | 28 | 17 | 0.21 |
| 5 | 545 | 598 | 57 | 19 | 0.43 |
| 6 | 560 | 596 | 71 | 8 | 0.67 |
| 7 | 560 | 600 | 124 | 14 | 0.96 |
| 8 | 570 | 620 | 159 | 100 | 0.88 |
| 9 | 560 | 602 | 126 | 20 | 0.83 |
| 10 | 550 | 597 | 142 | 20 | 1.14 |
| 11 | 545 | 600 | 36 | 7 | 0.13 |
| 12 | 546 | 595 | 41 | 5 | 0.75 |
| 13 | 545 | 593 | 26 | 3 | 0.32 |
| 14 | 528 | 583 | 21 | 2 | 0.65 |
| 15 | 556 | 605 | 20 | 9 | 0.03 |
| 16 | 544 | 598 | 11 | 3 | 0.08 |
| 17 | 620 | 685 | 57 | 3 | 0.11 |
| 18 | 560 | 660 | 5 | 2 | 0.02 |
| 19 | 620 | 693 | 83 | 4 | 0.13 |
| 20 | 622 | 715 | 33 | 7 | 0.09 |
| 21 | 620 | 695 | 65 | 3 | 0.15 |
| 22 | 610 | 700 | 5 | 2 | <0.01 |
| 23 | 621 | 698 | 35 | 3 | 0.05 |
| 24 | 620 | 690 | 67 | 3 | 0.13 |
| 25 | 586 | 690 | 19 | 12 | <0.01 |
| 26 | 565 | 630 | 12 | 14 | <0.01 |
| 27 | 623 | 775 | 14 | 4 | <0.01 |
| 28 | 515 | 620 | 11 | 6 | 0.03 |
| 29 | 540 | 595 | 28 | 7 | 0.24 |
| 30 | 585 | 680 | 36 | 7 | 0.02 |
| 31 | 525 | 595 | 2 | 2 | <0.01 |
| 32 | 520 | 694 | 1 | 1 | <0.01 |
| 33 | 420 | 570 | 4 | 2 | 0.07 |
| 34 | 430 | 574 | 4 | 1 | 0.09 |
| 35 | 455 | 568 | 5 | 1 | 0.12 |
| 36 | 375 | 535 | 2 | 1 | 0.19 |
| 37 | 390 | 535 | 4 | 1 | 0.09 |
| 38 | 425 | 565 | 5 | 2 | 0.10 |

EXAMPLE 5

5 μl of a solution of Dye No. 1 (2 mg/ml in 0.9% saline) was added to 100 μl of fresh whole blood (EDTA). The mixture was shaken and a wet slide immediately prepared for examination under a fluorescence microscope (540 nm broadband excitation filter, 590 nm long pass emission filter; 400× magnification). The nuclei of the peripheral blood leukocytes (PBLs) were observed as having been stained an intense orange color against a black background. In addition, moderately intensely stained platelets were observed. No To 100 μl of phage suspensions (PICM, $5 \times 10^9$ pfu/ml; T6, $4 \times 10^8$ pfu/ml; $2 \times 10^{10}$ pfu/ml) was added 10 μl of a solution of Dye No. 1 (1.6 mg/ml in 0.9% saline; sterile filtered through a 0.3 μm filter). The mixture was shaken and a wet slide prepared and examined under a fluorescence microscope as described in Example 5. PICM and T6 could be observed as small pinpoints of orange light against a black background.

EXAMPLE 9

Stock solutions of DNA and Dye No. 1 in 50 nM phosphate buffer pH 6.8 were mixed so that the final concentrations were 1–100 nM DNA base pairs and 1

μM dye in a final volume of 2 ml. The fluorescence of the solutions were measured on a Perkin-Elmer MPF 43A. Excitation was at 555 nM (4 nM bandpass); emission was at 605 nM (4 nM bandpass). A linear curve of fluorescence versus DNA concentration was obtained over this range.

EXAMPLE 10

To 0.5 ml of a solution of Dye No. 28 (50 μg/ml in 0.9% saline; sterile filtered through a 0.3 μM filter) was added 5 μl of fresh whole blood (EDTA). The mixture was shaken and a wet slide prepared and examined under a fluorescence microscope (450–490 nM broadband excitation, 530 nM long pass emission filter; 400× magnification). The nuclei of the peripheral blood leukocytes were stained bright orange, the endoplastic reticulum stained yellow, the cytoplasm and the membrane stained green. The platelets were stained orange. Erythrocytes and reticulocytes can easily be distinguished by the intensely stained yellow-orange reticulum of the reticulocytes and the weakly stained greenish membrane of erythrocytes.

EXAMPLE 11

The procedures described in Example 10 were repeated using a solution of Dye No. 33. The nuclei and endoplasmic reticulum of the peripheral blood leukocytes were stained intensely yellow, the cytoplasm and the membrane were stained intensely green-yellow. Erythrocytes and reticulocytes can also be distinguished easily by the intensely stained yellowish reticulum of the reticulocytes and the plain green-yellow stained membrane of erythrocytes.

EXAMPLE 12

A parafin embedded tissue slide was washed in xylene for ten minutes, then fixed in methanol for five minutes and then air dried. The tissue slide was stained by dipping the slide into a solution containing 10 μg/ml of Dye No. 28 in 0.1M phosphate buffer at pH 4, for ten to thirty seconds and then rinsing the slide briefly with water. The slide is air dried and then mounted under a plastic mounting medium. When observed under a fluorescence microscope using blue light excitation, the stained tissue exhibited metacrhomic effects. The nucleus was generally stained a deep orange color and the chromatin structure was readily observed. The cell cytoplasm was stained an intense green. In addition to clearly showing this distinguishing metachromatic effect, there was no evidence of fading or bleaching.

EXAMPLE 13

A blood smear was fixed in methanol for ten minutes and allowed to air dry. The fixed blood smear was stained for ten to fifteen minutes in a solution containing 100 μg/ml of Dye No. 28 in distilled water. The stained blood smear was rinsed briefly with water and then air dried. When the stained blood smear was observed under a fluorescence microscope and excited with blue light, the erythrocyte and leukocyte cytoplasm was stained green, platelets were stained yellow and the nuclei of the leukocytes were stained orange. There was no evidence of fading or bleaching.

It should be evident from the foregoing examples, that dyes exhibiting the claimed utility can be used to detect an almost limitless variety of microscopic organisms in biological samples. In particular, the dyes of the present invention are useful in distinguishing normal from abnormal cells. In addition to obvious uses in microfluorescence cytology, these dyes could be used in flow cytofluorimetry instruments to screen urine and water samples from elevated levels of bacteria. Representative of the biological structures which form complexes with the compounds of the present invention include DNA containing mammalian cells, platelets, DNA viruses, RNA viruses, yeasts, fungi and the like. In addition, whole blood samples also may be analyzed to provide a profile of components in view of the fact that these dyes will fluorescently stain reticulocytes, leukocytes and platelets.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of detecting nucleic acids in a biological sample which comprises contacting said biological sample with an effective amount of a dye of the formula:

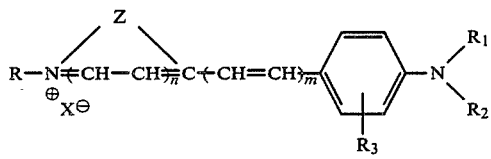

wherein n represents an integer having a value of 0 or 1;
m represents an integer having a value of 1 or 2;
R represents a member selected from the group consisting of lower alkyl, lower hydroxyalkyl, dialkylaminoalkyl, pyrrolidinoalkyl and morpholinoalkyl;
$R_1$ and $R_2$ independently represent a member selected from the group consisting of hydrogen, lower alkyl and lower haloalkyl;
$R_3$ represents a member selected from the group consisting of hydrogen, lower alkyl, lower alkoxy and amino;
Z represents nonmetallic atoms necessary to complete a heterocyclic nucleus selected from the group consisting of a benzothiazole nucleus, indolenine nucleus, naphthothiazole nucleus, benzoselenazole nucleus, benzoxazole nucleus, quinoline nucleus, and pyridine nucleus any of which may be substituted with lower alkyl, halo, nitro, amino and dialkylamino; and
X represents an anion; thereby producing a complex between the dye and the nucleic acids; irradiating the complex with light of excitation wavelength thereby causing the complex to emit fluorescence; and measuring the emitted fluorescence.

2. A method according to claim 1 wherein n is 0; R is dialkylaminoalkyl and Z represents nonmetallic atoms necessary to complete a heterocyclic nucleus selected from the group consisting of a benzothiazole nucleus, a naphthothiazole nucleus, a benzoselenazole nucleus, a benzoxazole nucleus and substituted benzothiazole, naphthothiazole, benzoselenazole, benzoxazole nucleus wherein the substituent is selected from the class consisting of lower alkyl, halo and amino.

3. A method according to claim 2 wherein the nucleic acid is DNA.

4. A method according to claim 3 wherein m is 1; $R_1$ and $R_2$ are lower alkyl, $R_3$ is hydrogen and Z represents nonmetallic atoms necessary to complete a heterocyclic nucleus selected from the group consisting of benzothiazole nucleus, a naphthothiazole nucleus, a benzoselenazole nucleus and substituted benzothiazole, naphthothiazole and benzoselenazole nucleus wherein the substitutent is selected from the class consisting of lower alkyl, halo and amino.

5. A method according to claim 4 wherein X is selected from the group consisting of halogen, methylsulfate and perchlorate.

6. A method according to claim 5 wherein the dye is 3-γ-dimethylaminopropyl-2-p-dimethylaminostyryl-benzothiazolium iodide.

7. A method according to claim 5 wherein the dye is 3-γ-dimethylaminopropyl-5-chloro-2-dimethylaminostyrylbenzothiazolium iodide.

8. A method according to claim 5 wherein the dye is 3-γ-dimethylaminopropyl-2-p-dimethylaminostyryl-α-naphthothiazolium iodide.

9. A method according to claim 5 wherein the dye is 3-γ-dimethylaminopropyl-2-p-dimethylaminostyryl-benzoselenazolium iodide.

10. A method according to claim 5 wherein the dye is 3-γ-dimethylaminopropyl-5-methyl-2-p-dimethylaminostyrylbenzothiazolium iodide.

11. A method of staining tissues and fixed cells in a biological sample which comprises contacting said biological sample with an effective amount of a dye of the formula:

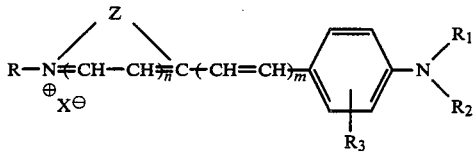

wherein n represents an integer having a value of 0 or 1;
m represents an integer having a value of 1 or 2;
$R_1$ and $R_2$ independently represent a member selected from the group consisting of hydrogen, lower alkyl and lower halo alkyl;
$R_3$ represents a member selected from the group consisting of hydrogen, lower alkyl, lower alkoxy and amino;
Z represents nonmetallic atoms necessary to complete a pyridine nucleus;
R represents dialkylaminoalkyl; and
X represents an anion, thereby producing a dye complex, irradiating the complex with light of excitation wavelength thereby causing the complex to emit fluorescence; and measuring the emitted fluorescence.

12. A method according to claim 11 wherein m is 1, $R_1$ and $R_2$ are lower alkyl and $R_3$ is hydrogen.

13. A method according to claim 12 wherein n is 1.

14. A method according to claim 13 wherein the dye is 1-γ-dimethylaminopropyl-4-p-dimethylaminostyryl-pyridinium iodide.

15. A method of staining cells in suspension in a biological sample which comprises contacting said biological sample with an effective amount of a dye of the formula:

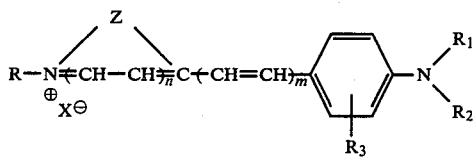

wherein n represents an integer having a value of 0 or 1;
m represents an integer having a value of 1 or 2;
$R_1$ and $R_2$ independently represent a member selected from the group consisting of hydrogen, lower alkyl, and lower haloalkyl;
$R_3$ represents a member selected from the group consisting of hydrogen, lower alkyl, lower alkoxy and amino;
Z represents nonmetallic atoms necessary to complete an aminopyridine nucleus;
R represents lower alkyl; and
X represents an anion; thereby producing a dye complex, irradiating the complex with light of excitation wavelength thereby causing the complex to emit fluorescence; and measuring the emitted fluorescence.

16. A method according to claim 15 wherein m is 1, $R_1$ and $R_2$ are lower alkyl and $R_3$ is hydrogen.

17. A method according to claim 16 wherein n is 1.

18. A method according to claim 17 wherein the dye is 1-methyl-2-amino-4-p-dimethylaminostyryl-pyridinium iodide.

* * * * *